(12) United States Patent
Marks et al.

(10) Patent No.: US 10,857,316 B2
(45) Date of Patent: Dec. 8, 2020

(54) PERSONAL VAPORIZER

(71) Applicant: Stoned Free LLC, Winchester, OR (US)

(72) Inventors: Heidi Marks, Winchester, OR (US); Peter Crawford, Winchester, OR (US); James Schwartz, Winchester, OR (US)

(73) Assignee: STONED FREE LLC, Winchester, OR (US)

( * ) Notice: Subject to any disclaimer, the term of this patent is extended or adjusted under 35 U.S.C. 154(b) by 296 days.

(21) Appl. No.: 15/946,193

(22) Filed: Apr. 5, 2018

(65) Prior Publication Data

US 2018/0221605 A1   Aug. 9, 2018

Related U.S. Application Data

(63) Continuation-in-part of application No. 15/893,272, filed on Feb. 9, 2018.

(60) Provisional application No. 62/456,703, filed on Feb. 9, 2017.

(51) Int. Cl.
| | |
|---|---|
| *A61M 15/06* | (2006.01) |
| *A61M 11/04* | (2006.01) |
| *A24F 47/00* | (2020.01) |
| *A61M 15/00* | (2006.01) |
| *A61M 11/00* | (2006.01) |

(52) U.S. Cl.
CPC ........... *A61M 15/06* (2013.01); *A24F 47/008* (2013.01); *A61M 11/003* (2014.02); *A61M 11/042* (2014.02); *A61M 15/0021* (2014.02); *A61M 2205/3653* (2013.01); *A61M 2205/8206* (2013.01)

(58) Field of Classification Search
None
See application file for complete search history.

(56) References Cited

U.S. PATENT DOCUMENTS

| | | |
|---|---|---|
| 9,078,475 B2 | 7/2015 | Li et al. |
| 9,271,529 B2 | 3/2016 | Alima |
| 9,603,390 B2 | 3/2017 | Li et al. |
| 9,648,909 B2 | 5/2017 | Zhou et al. |
| 9,861,129 B2 | 1/2018 | Liu et al. |
| 9,861,132 B2 | 1/2018 | Li et al. |
| 2013/0087160 A1* | 4/2013 | Gherghe ............... A24F 1/00 131/329 |

(Continued)

*Primary Examiner* — Phu H Nguyen
(74) *Attorney, Agent, or Firm* — Panitch Schwarze Belisario & Nadel LLP

(57) ABSTRACT

A vaporizer pen for heating and vaporizing a liquid product that is ingested by a user has an outer hollow tube with a proximal end and a distal end and an inner hollow tube within the outer hollow tube having a proximal end and a distal end. The inner tube defines a chamber inside. A mouthpiece abuts the proximal end of the outer hollow tube and an atomizing chamber is positioned within the outer hollow tube and abuts the distal end of the inner hollow tube. A porous stone has a proximal stone end and a distal stone end and is configured to retain the liquid product. The porous stone is positioned within the hollow inner tube and the distal stone end is in contact with the atomizing chamber. A heating element is in communication with the atomizing chamber and is constructed of a ceramic material.

2 Claims, 5 Drawing Sheets

(56) References Cited

U.S. PATENT DOCUMENTS

| | | |
|---|---|---|
| 2015/0257447 A1* | 9/2015 | Sullivan ................ A24F 47/008 131/329 |
| 2015/0258288 A1 | 9/2015 | Sullivan |
| 2015/0359261 A1 | 12/2015 | Li et al. |
| 2017/0136196 A1 | 5/2017 | Davidson et al. |
| 2017/0188636 A1 | 7/2017 | Li et al. |
| 2017/0367411 A1 | 12/2017 | Duc |
| 2018/0014576 A1 | 1/2018 | White |
| 2018/0020722 A1 | 1/2018 | Davis et al. |

* cited by examiner

PERSONAL VAPORIZER

CROSS-REFERENCE TO RELATED APPLICATIONS

The present application is a Continuation-in-Part of U.S. patent application Ser. No. 15/893,272 filed Feb. 9, 2018 titled "Personal Vaporizer" which claims priority to U.S. Patent Application No. 62/456,703, filed Feb. 9, 2017 and entitled "Personal Vaporizer."

BACKGROUND OF THE INVENTION

The preferred subject invention is related to an electronic cigarette, personal vaporizer (PV), vaporizer pen and like devices. A vaporizer or vaporizer pen is a device that heats and vaporizes a liquid material such as a liquid tobacco or an herbal extraction product without causing combustion. Such devices typically vaporize a liquid material ("vaping substance") to produce a vapor or mist replicating the experience of smoking a cigarette, pipe or cigar.

Vaporizers have quickly become a popular method for inhaling tobacco or herbal extractions and are viewed by many consumers as a "healthier" alternative to smoking. In addition, because vaporizers do not combust the vaping substance, they are significantly more efficient than smoking in extracting the active compounds from the tobacco or herbal extraction product. Smoking has been shown to destroy as much as thirty percent (30%) of the active compounds the tobacco or herbal extraction product include.

Handheld vaporizers are generally constructed of a mouth piece, a filter, a chamber for a tobacco or herbal extraction cartridge, a heating chamber, an indicator light, and a battery. The typical vaporizer contains an atomizing device with a small, porous body usually approximately one millimeter (1 mm) in diameter by about three to five millimeters (3-5 mm) in length, that extends into the reservoir and is used to wick the tobacco, essential oil extractions or herbal extractions and deliver it to a heating element (usually a metal coil) that is typically either wrapped around or inserted into the porous body. When the consumer presses the power button, the heating element activates, heating the liquid solution or plant material to create the vapor.

These traditional vaporizers subject the tobacco or herbal liquid and vapor to contact with a metal coil, in addition to other components like solder joints, in the heating process. Such heating methods can allow metallic particles to fleck off from these metal components into the vapor when heated. Due to the small size of such particles, they can travel deep into the lungs during inhalation. A need, therefore, exists for a vaporizer with a design that isolates any metallic components from the tobacco or herbal extraction product to prevent metallic particles from flecking off and being inhaled into a user's lungs.

Traditional vaporizers also typically utilize a cotton or plastic wick to draw the tobacco, essential oil extractions or herbal extractions to the heat source. In such configurations, particles from the wick itself can also be drawn into the vapor and into the user's lungs. A need, therefore, also exists for a vaporizer with an alternate, inert material to draw in the tobacco or herbal extractions to be heated and vaporized without permitting particles from the wick to be inhaled. The preferred present invention addresses the described limitations of prior art vaporizer pens.

BRIEF SUMMARY OF THE INVENTION

Applicant has identified silicon carbide or like inert porous stones as the ideal or preferred material for use in a personal vaporizer ("PV") device. Not only does the preferred PV device minimize, or eliminate, the above hazards but it also acts as a natural material for wicking the essential oil extractions, herbal extractions and other liquid components used in the PV device from their place of storage to a heater used to vaporize such materials.

One aspect of the present invention relates to a vaporizer pen for heating and vaporizing a liquid product that is ingested by a user, the vaporizer pen having an outer hollow tube with a proximal end and a distal end. An inner hollow tube is positioned within the outer hollow tube having a proximal end and a distal end. The inner tube defines a chamber inside. A mouthpiece abuts the proximal end of the outer hollow tube, an atomizing chamber is positioned within the outer hollow tube and abuts the distal end of the inner hollow tube and a porous stone has a proximal stone end and a distal stone end. The porous stone is configured to retain the liquid product. The porous stone is positioned within the hollow inner tube. The distal stone end in contact with the atomizing chamber and a heating element is in communication with the atomizing chamber. The heating element is constructed of a ceramic material.

Another aspect of the preferred present invention relates to a vaporizer pen for heating and vaporizing a liquid product that is ingested by a user. The vaporizer pen has a hollow tube with a proximal end and a distal end, a mouthpiece abutting the proximal end of the hollow tube and an atomizing chamber within the hollow tube. The atomizing chamber is positioned near the distal end of the hollow tube. A porous stone has a proximal stone end and a distal stone end. The porous stone is configured to retain the liquid product and has a channel or hole within the porous stone running from the proximal stone end to the distal stone end. The porous stone is positioned within the hollow tube. The distal stone end is in contact with or within the atomizing chamber and a heating element is in communication with the atomizing chamber. The heating element is constructed of a ceramic material.

BRIEF DESCRIPTION OF THE SEVERAL VIEWS OF THE DRAWINGS

The foregoing summary, as well as the following detailed description of the preferred invention, will be better understood when read in conjunction with the appended drawings. For the purpose of illustrating the preferred invention, there are shown in the drawings embodiments which are presently preferred. It should be understood, however, that the invention is not limited to the precise arrangements and instrumentalities shown. In the drawings.

DETAILED DESCRIPTION OF THE INVENTION

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The basic components of prior art VP devices usable for vaporizing substances that can be inhaled are an outer housing or vape pen containing a reservoir holding a liquid that can be vaporized and a heating element to vaporize the liquid. Means to transfer the liquid from the reservoir are also needed. But to modulate the amount of vapor emitted from the VP device to the user, other controls must be added for controlling the heater temperature and amount of vaporable substances in contact with the heater.

All components in contact with the vaporizable liquid in the prior art devices have the potential for shedding unwanted substances or vapors into the air stream conveying the vaporizable materials to the user. Thus, there is a need for materials usable in the VP device that will eliminate or reduce these unwanted components. To minimize these concerns, in the preferred present invention, all components and surfaces that come in contact with vapors or vaporizable liquid are made from or coated with inert, porous stone such as silicon carbide or other generally inert materials or coatings that limit or prevent nanoparticles from being introduced into the vaporized liquid mist or material.

In the prior art devices, the typical components in contact with the vapors are the liquid storage component and the heater. In the preferred present invention, each of these is coated with, or made of, inert, porous stone such as silicon carbide or other related materials to prevent adverse reaction to the user. These elements are contained within the outer housing of the pen.

Figure 1:
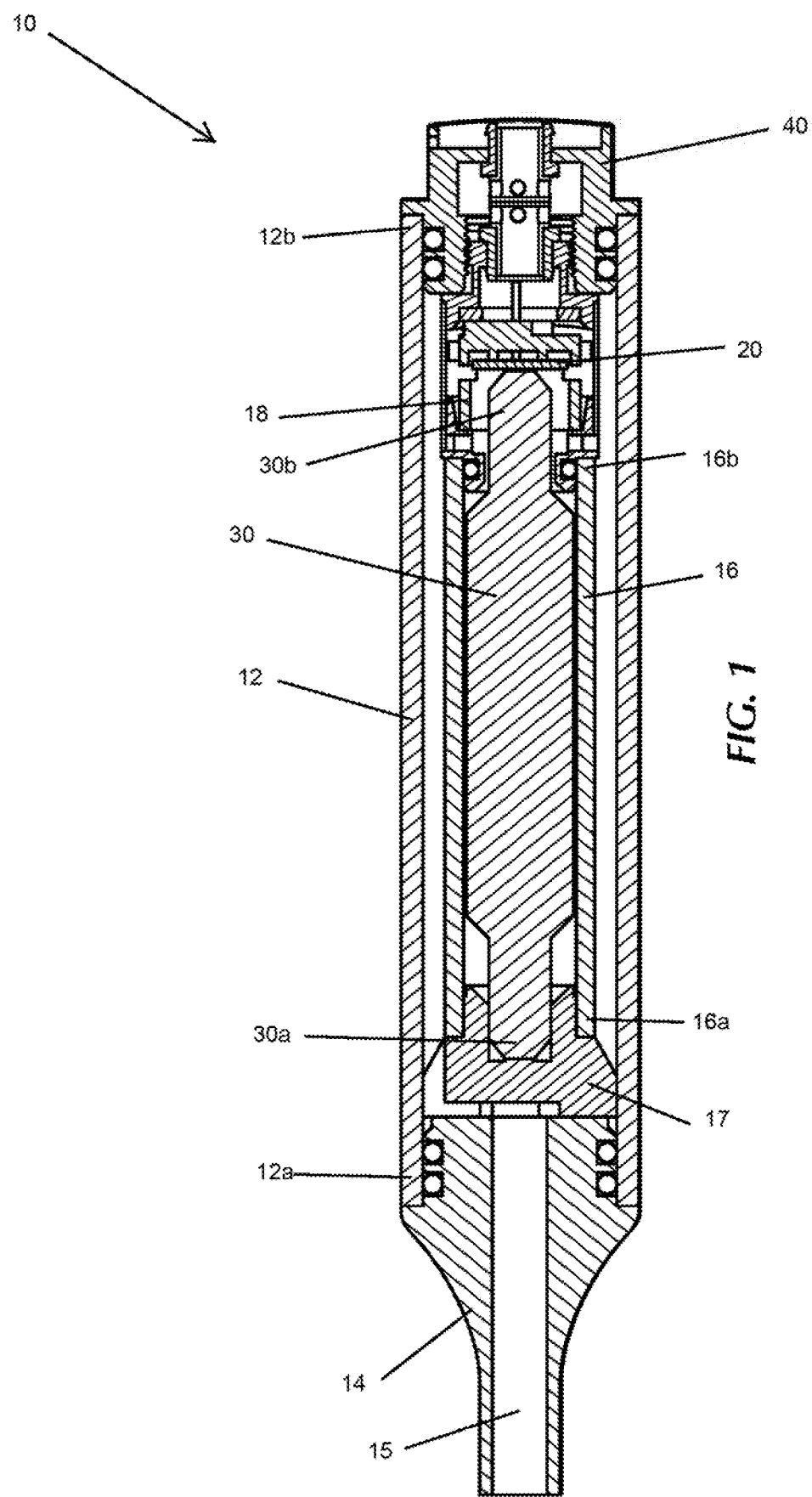
FIG. 1 is a cross-sectional view of a portion of a vaporizer pen in accordance with a first preferred embodiment of the present invention.
Figure 2:
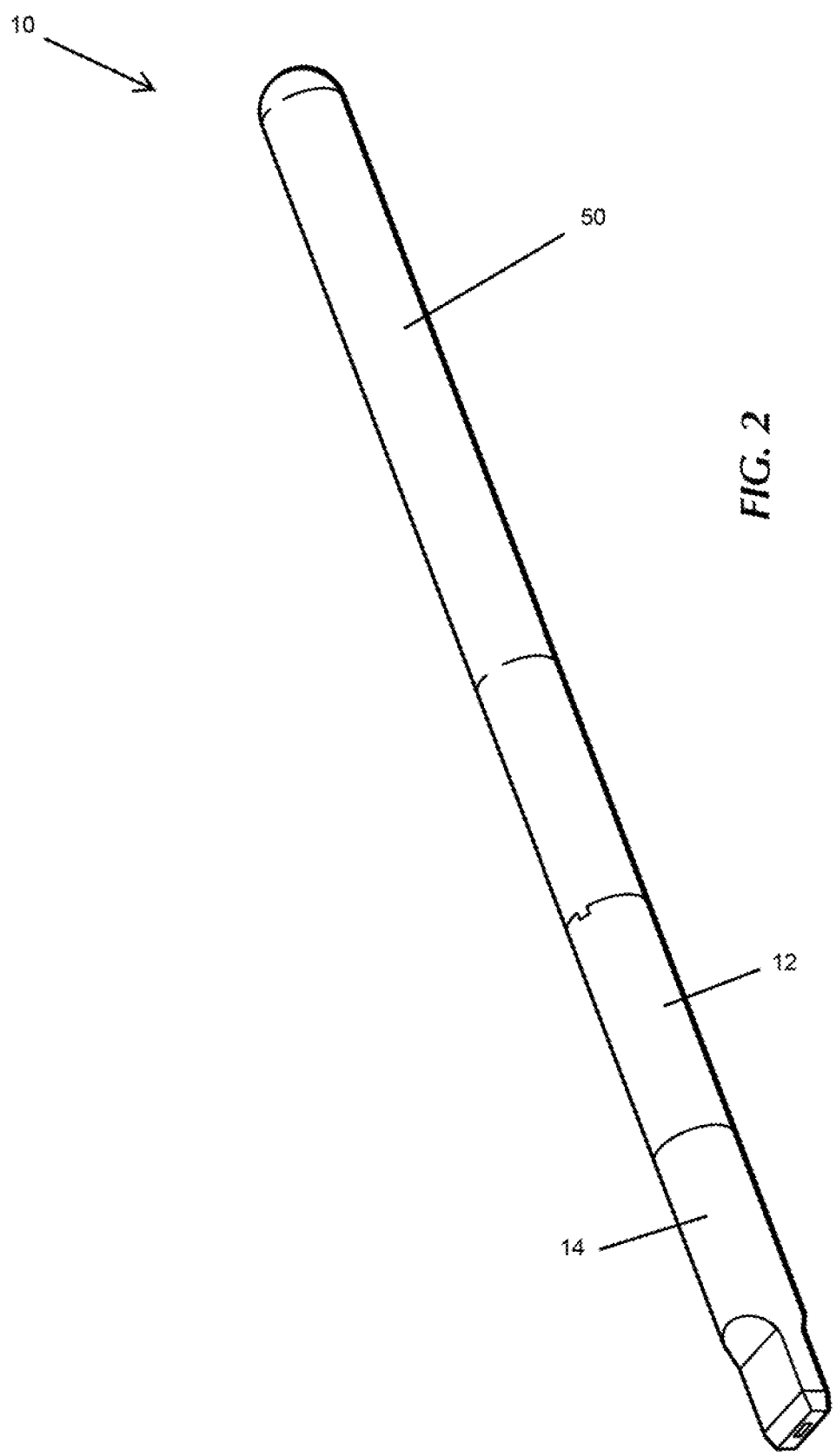
FIG. 2 is a side perspective view of the vaporizer pen of FIG. 1 mated with a battery portion.
Figure 3:
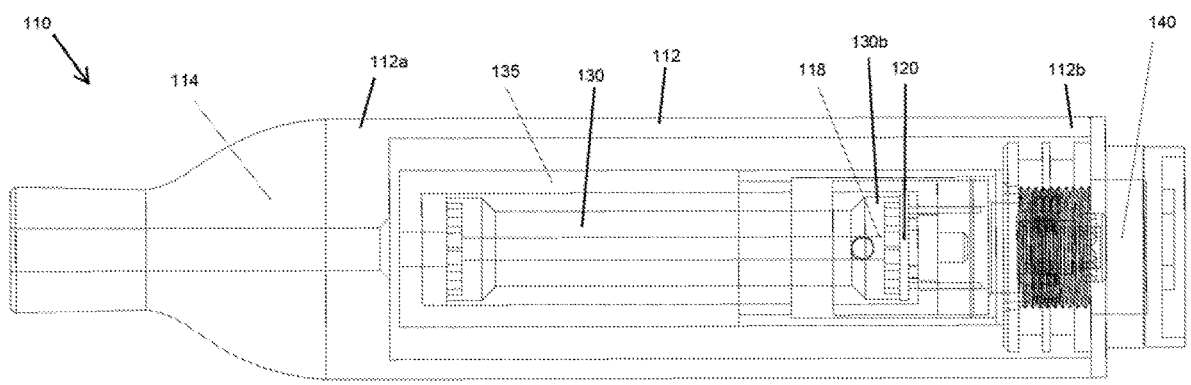
FIG. 3 is a partially opaque side elevational view of a portion of a vaporizer pen in accordance with a second preferred embodiment of the present invention.

Referring to FIGS. 1 and 2, a first preferred embodiment of the present invention (i.e., a vaporizer pen 10) removes exposed metal coils and cotton wicks of prior art VP devices, with their contaminants, from harm. A heating element 20 is a preferably a ceramic plate providing a relatively safe form of heat transfer to the oil or extraction delivery mechanism. The oil or extraction delivery mechanism is preferably a porous stone 30, which may be constructed of a silicon carbide ("SiC"), diatom stone or other inert, safe, porous stone or rock. The porous stone 30 holds and meters the vaping oil or extractions into contact with the heating element 20 rather than using the outdated and unhealthy metal coil/cotton wick system of the prior art VP devices. Herbal or E-Cig oil is absorbed by SiC porous stone 30 and other inert porous materials and, when heated, releases the oil vapor in the cleanest delivery method possible, other than pure medical nebulization devices. The heating element 20 may also take on other shapes, such as a cup, to maximize the transfer of heat by creating additional surface area contact between the heating element 20 and the liquid stored in the vaporizer pen 10. The heating element 20 may also wrap the extraction delivery mechanism or porous stone 30 with heat either through direct contact with elements of the heating element 20 to the stone 30 or by close proximity to the porous stone 30 in such a fashion as to warm the liquid, essential oil extractions or herbal extractions within the stone 30, thereby providing a more uniform and complete vaporization of the liquid, essential oil extractions, herbal extractions or oil.

The first preferred embodiment of the vaporizer pen 10 is more specifically, and preferably, constructed of an outer hollow tube 12 having a proximal end 12a and a distal end 12b. The first preferred embodiment of the vaporizer 10 also contains an inner hollow tube 16 positioned within the outer hollow tube 12, such that space is left for the passage of air and vapor between the outer hollow tube 12 and the inner hollow tube 16. The outer hollow tube 12 is preferably at least partially opaque or opaque such that a user is able to visually detect the vapor or mist flowing from the distal end 12b to a mouthpiece 14 where the vapor or mist are ingested. The inner hollow tube 16 also preferably contains a proximal end 16a and a distal end 16b. The outer hollow tube 12 and inner hollow tube 16 are preferably constructed of any non-metal material, preferably an inert material, suitable for achieving the purpose of the present invention, and are even more preferably constructed of glass.

The mouthpiece 14 is preferably located abutting the proximal end 12a of the outer hollow tube 12. The mouthpiece 14 preferably contains a hollow or channel 15 through its center for transfer of the vapor from the channel between the hollow outer tube 12 and the inner tube 16 to the mouth of the user. The mouthpiece 14 may include diametrically spaced holes or channels therein that permit flow of the vaporized liquid from the channel between the outer hollow tube 12 and the inner tube 16 to the mouthpiece channel 15. The mouthpiece 14 is also preferably removable from the outer hollow tube 12 and a portion of the mouthpiece 14 preferably extends into the outer hollow tube 12 with gaskets to secure the mouthpiece 14 to the hollow outer tube 12. The first preferred embodiment of the vaporizer pen 10 may also contain a fixture 17 positioned within the outer hollow tube 12 and between the proximal end 16a of the inner hollow tube 16 and the portion of the mouthpiece 14 extending into the outer hollow tube 12. The fixture 17 is preferably constructed of silicon, but may also be constructed of any other non-metal and preferably inert material. The fixture 17 may also include channels or holes therein that facilitate flow of the vaporized liquid to the mouthpiece channel 15.

An atomizing chamber 18 is preferably positioned within the outer hollow tube 12 and preferably abuts the distal end 16b of the inner hollow tube 16. The first preferred embodiment of the vaporizer 10 also preferable contains a relatively solid or continuous porous stone 30 having a proximal stone end 30a and a distal stone end 30b. The porous stone 30 is preferably constructed of silicon carbide, and most preferably is a composition of ninety-eight and three tenths percent (98.3%) silicon carbide, three tenths percent (0.3%) strontium carbonate, two tenths percent (0.2%) iron oxide, three hundredths percent (0.03%) magnetic substances, and fourteen hundredths percent (0.14%) Teflon®, but may also be constructed of any porous, non-metal material and preferably inert material capable of retaining a liquid herbal extraction, essential oil extractions or tobacco oil. The porous stone 30 is preferably positioned within the inner hollow tube 16, with its distal stone end 30b in contact with and/or within the atomizing chamber 18 and with its proximal stone end 30a abutting or extending into the fixture 17. The proximal stone end 30a is preferably narrowed relative to a central section and the distal stone end 30b is also preferably narrowed relative to the central section. The narrowed or nippled proximal and distal stone ends 30a, 30b are preferably configured and arranged for engagement by the fixture 17 and the atomizing chamber 18 or other mounting structure, while the central section is preferably larger or wider for maximizing the volume of material to carry or absorb the liquid herb, tobacco or related material. The proximal and distal stone ends 30a, 30b are not limited to being narrowed or nippled and may have generally the same size or a larger size compared to the central section. The first preferred embodiment of the vaporizer 10 also preferably contains a heating element 20 in communication with and/or positioned within the atomizing chamber 18. The heating element 20 is preferably constructed of a ceramic material, and even more preferably is constructed of silicon carbide. The heating element 20 is preferably cup-shaped so as to cup the distal stone end 30b, but may also be disc shaped or any other shape suitable for transferring heat to the porous stone 30.

The first preferred embodiment of the vaporizer 10 also preferably contains a battery fixture 40 positioned within or abutting the distal end 12b of the outer hollow tube 12. The battery fixture 40 is preferably configured so as to physically, removably and electrically connect to a battery 50 for powering the vaporizer 10. In addition, the mouthpiece 14, fixture 17, the inner tube 16 and the stone 30 are preferably removable and replaceable from the outer tube 12 and the remainder of the vapor pen 10 such that the porous stone 30 may be removed and replaced with a fully infused porous stone 30 after another porous stone 30 is depleted or exhausted of liquid material for vaporization.

In use, the user of the first preferred embodiment of the vaporizer 10 may activate the battery 50 to heat the heating element 20 and vaporize the liquid herbal extraction, essential oil extractions or tobacco oil in the porous stone 30. When the user places his or her mouth on the mouthpiece 14 and inhales, the heated oil, essential oil extractions or herbal extractions is transferred from the stone 30 and atomizing chamber 18, between the outer hollow tube 12 and inner hollow tube 16, to the mouthpiece 14, through the mouthpiece channel 15 and into the user's mouth.

Referring now to FIGS. 3-7, a second preferred embodiment of a vaporizer pen 110 in accordance with the present invention includes a hollow tube 112 having a proximal end 112a and a distal end 112b. Within or abutting the distal end 112b of the hollow tube 112 is a battery fixture 140 capable of being physically, removably and/or electrically connected to a battery unit (not shown in the second embodiment). The second embodiment also preferably includes a ceramic heating element 120 located within an atomizing chamber 118. The second preferred embodiment also includes a porous stone 130 located within the hollow tube 112. Preferably, the porous stone 130 contains a distal end 130b positioned within the atomizing chamber 118 and abutting the heating element 120. The porous stone 130 is preferably enclosed by a stone chamber 135 formed within the hollow tube 112, which can be affixed to the atomizing chamber 118. The second preferred embodiment also preferably includes a mouthpiece 114 for attachment to the proximate end 112 of the hollow tube 112. The second preferred stone 130 is also preferably removable from and replaceable within the hollow tube 112, such that a depleted stone 130 may be removed and replaced with a fully infused stone 130 by the user.

Figure 4:
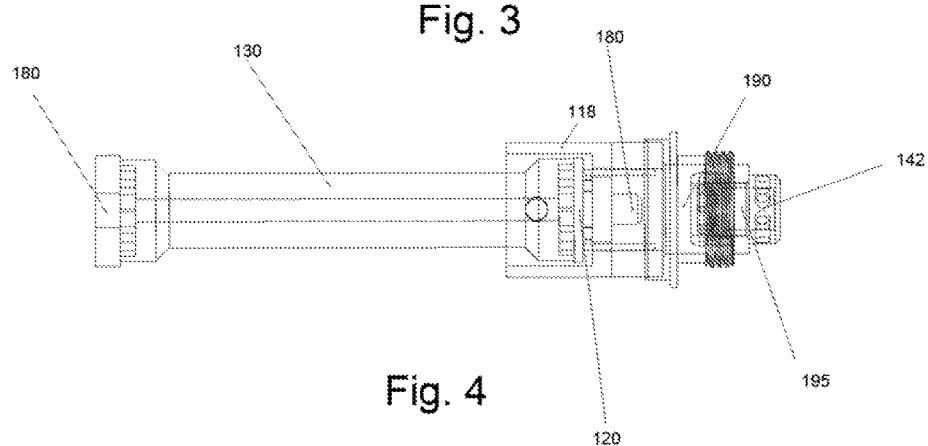
FIG. 4 is a partially opaque side elevational view of a portion of the vaporizer pen of FIG. 3.

FIG. 4 shows a portion of the vaporizer pen 110 with the mouthpiece 114 and outer tube 112 removed. The vaporizer pen 110 preferably includes silicon spacers 180 and fixtures 190 for maintaining the various components in their proper alignment, as well as an insulating ring 195 to maintain the vapor in the proper locations and prevent harmful particles from entering the vapor. An electrode 142 is preferably a part of the battery fixture 140 and provides electrical conductivity between the battery fixture 140 and the battery (not shown).

Figure 5:
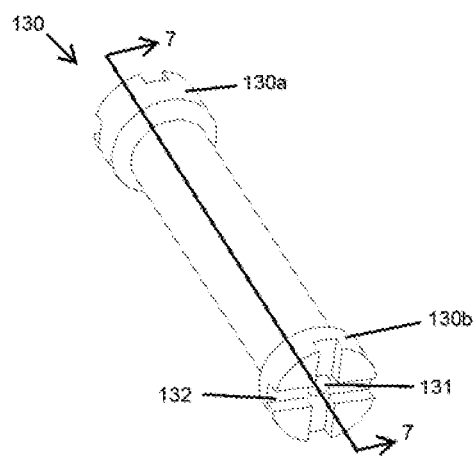
FIG. 5 is a top perspective view of a porous stone for retaining liquid tobacco, essential oil extractions or herbal extractions in accordance with the vaporizer pen of FIG. 3.
Figure 6:
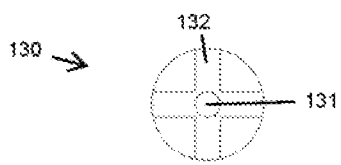
FIG. 6 is a top plan view of the porous stone of FIG. 5.
Figure 7:
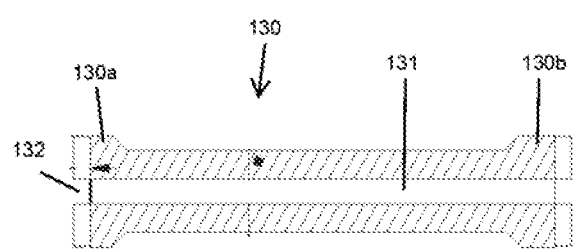
FIG. 7 is a cross-sectional view of the porous stone of FIG. 5, taken along line 7-7 of FIG. 5.
Figure 8:
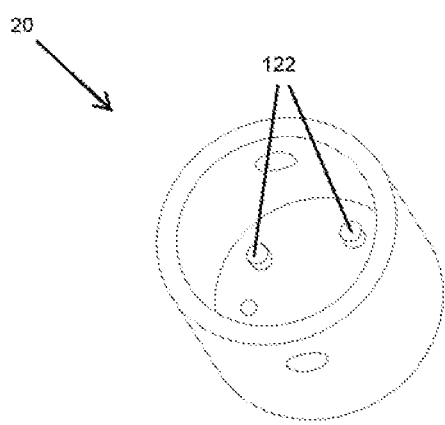
FIG. 8 is a top perspective view of a heating element designed for mating with and heating the porous stone of FIG. 5, in accordance with the vaporizer pen of FIG. 3.

Referring to FIGS. 5-7, the porous stone 130 of the second preferred embodiment includes wider proximal and distal ends 130a, 130b than its central section. The proximal and distal ends 130a, 130b are preferably mirror images of each other with a neck that expands to a generally consistent diameter that is greater than the diameter of the central section. The porous stone 130 preferably fills the width of the stone chamber 135 at the proximal and distal ends 130a, 130b. The second preferred embodiment of the porous stone 130 includes a hole or channel 131 running through the center of the porous stone 130 from the proximal stone end 130a to the distal stone end 130b. Preferably, the heating element 20 is configured with protrusions 122, as shown in FIG. 8, capable of mating with depressions 132 present in the distal stone end 130b, as well as in the proximal stone end 130a, such that the preferred stone 130 may be inserted with either end 130a, 130b in the heating element 20 in an assembled configuration. The mating of the protrusions 122 and depressions 132 securely mount the porous stone 130 to the heating element 20 and, preferably, facilitates engagement between the sidewalls of the heating element 20 and outer side walls of the distal end 130b of the porous stone 130. In use, the second preferred embodiment of the vaporizer pen 110 functions much like the first preferred embodiment, except that the vapor travels through the hole 131 of the porous stone 130 to the mouthpiece 114 into the mouthpiece channel 115 rather than between inner and outer hollow tubes.

The added benefit of using SiC or other inert porous material for the stones 30, 130 is the benefit to the environment in combination with the ability to absorb and retain the liquid for vaporization. Silicon Carbide is an environmentally friendly safe stone that can be disposed in your gravel driveway or in your stone landscaping, or it can be returned and exchanged for a new stone or deposit value. The porous reservoir constructed of SiC is one hundred percent (100%) reusable and will save the planet countless tons of carbon emissions and land fill material.

One additional benefit of the SiC wick system is easy retrieval of any unused oil, essential oil extractions or herbal extractions from the SiC wick reservoir because the porous stone's 30 matrix retains and reclaims oil, essential oil extractions or herbal extractions until it is exposed to heat from the heating element 20, to ensure that no oil, essential oil extractions or herbal extractions is wasted. The disclosed SiC porous stone 30, 130 wick system was designed to wick at both ends to ensure the complete dispersion of oil, essential oil extractions or herbal extractions onto the heating element 20.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A vaporizer pen for heating and vaporizing a liquid or oil extraction product that is ingested by a user, the vaporizer pen comprising:

a hollow tube having a proximal end and a distal end;

a mouthpiece abutting the proximal end of the hollow tube;

an atomizing chamber within the hollow tube, the atomizing chamber near the distal end of the hollow tube;

a porous stone having a proximal stone end and a distal stone end, the porous stone configured to retain the liquid product and having a channel or hole within the porous stone running from the proximal stone end to the distal stone end, the porous stone positioned within the hollow tube, the distal stone end in contact with or within the atomizing chamber and having depressions; and a heating element in communication with the atomizing chamber, the heating element constructed of a ceramic material and having protrusions, the protrusions engaging the depressions in an assembled configuration.

2. The vaporizer pen of claim 1, wherein the proximal stone end has a proximal stone end diameter and the proximal stone has a central section with a central diameter, the central diameter being smaller than the proximal stone end diameter.

\* \* \* \* \*